United States Patent
Harada et al.

(10) Patent No.: US 6,191,191 B1
(45) Date of Patent: Feb. 20, 2001

(54) POLYMERIZABLE DENTAL COMPOSITION

(75) Inventors: Miho Harada; Kenichi Hino, both of Kurashiki (JP)

(73) Assignee: Kuraray Co., Ltd., Kurashiki (JP)

( * ) Notice: Under 35 U.S.C. 154(b), the term of this patent shall be extended for 0 days.

(21) Appl. No.: 09/147,661

(22) PCT Filed: Jun. 4, 1998

(86) PCT No.: PCT/JP98/02488

§ 371 Date: Feb. 9, 1999

§ 102(e) Date: Feb. 9, 1999

(87) PCT Pub. No.: WO98/56332

PCT Pub. Date: Dec. 17, 1998

(30) Foreign Application Priority Data

Jun. 9, 1997 (JP) .................................................. 9-150837

(51) Int. Cl.$^7$ ...................................................... A61K 6/08
(52) U.S. Cl. .................. 523/115; 523/116; 523/118; 522/64; 522/26; 522/28; 522/182
(58) Field of Search .................. 523/115, 116, 523/118; 522/64, 26, 28, 182

(56) References Cited

U.S. PATENT DOCUMENTS

| | | | | |
|---|---|---|---|---|
| 4,657,941 | * | 4/1987 | Blackwell et al. | 522/14 |
| 5,154,762 | * | 10/1992 | Mitra et al. | 523/116 |
| 5,321,053 | | 6/1994 | Hino et al. | 522/26 |
| 5,338,773 | * | 8/1994 | Lu et al. | 523/116 |
| 5,367,002 | * | 11/1994 | Huang et al. | 523/116 |
| 5,679,710 | * | 10/1997 | Davy et al. | 514/549 |
| 5,891,931 | * | 4/1999 | Leboeuf et al. | 522/64 |

FOREIGN PATENT DOCUMENTS

| | | | | |
|---|---|---|---|---|
| 548 740 | * | 6/1993 | (EP) | . |
| 246514 | * | 4/1987 | (JP) | . |
| 157126 | * | 6/1999 | (JP) | . |
| 19650 | * | 5/1998 | (WO) | . |

OTHER PUBLICATIONS

JP06016713A, Abstract, Jan. 25, 1994.*

* cited by examiner

*Primary Examiner*—Margaret Medley
(74) *Attorney, Agent, or Firm*—Oblon, Spivak, McClelland, Maier & Neustadt, P.C.

(57) ABSTRACT

A polymerizable composition for dental use, containing monomer (a) with a polymerizable olefinic unsaturated group, acylphosphine oxide (b), organic peroxide (c), tertiary amine (d) and aromatic sulfinic acid and/or a salt thereof (e). The polymerizable composition for dental use exerts excellent curability by any of photo-polymerization and chemical polymerization, having a good color for dental use, with less color change between prior to and after polymerization, and excellent light resistance, producing a cured product with a smaller thickness of the unpolymerized layer on the surface, having larger curing depth and excellent adhesion to teeth and metals and the like and great color fastness in hot water and in darkness. By taking advantages of these excellent properties, the polymerizable composition can effectively be used for utilities, for example as a bonding agent, a composite resin, an adhesive agent, a primer and an opaque primer and the like, for dental use.

8 Claims, No Drawings

POLYMERIZABLE DENTAL COMPOSITION

This Application is a 371 of PCT/JP98/02488 dated Jun. 4, 1998.

TECHNICAL FIELD

The present invention relates to a novel polymerizable composition for dental use, being polymerizable by any method of photo-polymerization and chemical polymerization, having less color change between prior to and after polymerization, generating cured products with great color stability and having good surface curability and a short polymerization time.

Taking advantages of the great characteristic properties of the polymerizable composition for dental use in accordance with the present invention, the composition can effectively be used as an adhesive, a bonding agent, a composite resin, a surface treating agent, an opaque primer and the like, for dental use.

TECHNICAL BACKGROUND

In recent years, polymerizable resin materials have been used as polymerizable compositions for dental use, widely in the entire fields of dental treatment, owing to the great processability such that the materials can appropriately be molded into desired shapes, the good aesthetic beauty such that the materials can restore damaged tooth as if the resulting tooth were natural, and the high strength of the cured product.

Since U.S. Pat. No. 3,066,112 issued in 1959 proposes the application of polyfunctional acrylic polymerizable resins to the treatment of caries, a great number of materials chemically polymerizable at ambient temperature have been put to practical use. Thereafter, a dental material of ultraviolet polymerization has been proposed by using benzoin methyl ether and similar catalysts, in parallel to the progress of materials of chemical polymerization (Japanese Patent Application Laid-Open No. 47-247).

Furthermore, a number of products have been developed, wherein a variety of polymerization processes have been applied, including a dental material of photo-polymerization using camphorquinone (Japanese Patent Application Laid-Open No. 48-49875).

Since then, photo-polymerizable materials containing camphorquinone have widely been used as filling materials for dental use.

For applications where no effective level of light is incident even after photo-irradiation, for example for bonding of metal crowns, inlay and onlay, furthermore, dental materials of chemical polymerization are currently used.

Additionally, Japanese Patent Application Laid-Open No. 60-32810 discloses a dental composition containing a catalyst system comprising one of α-diketone compounds, namely camphorquinone, an organic peroxide and an amine, and describes that the thickness of the resulting unpolymerized layer on the surface is small.

Further, Japanese Patent Application Laid-Open No. 60-89407 describes that a dental composition containing a catalyst system of the same composition as described above can attain very large curing depth.

These compositions for dental use, which contain a catalyst system comprising camphorquinone, organic peroxides and amines, have both the functions of chemical polymerization and photo-polymerization. Such composition shave been used widely as adhesives and bonding agents for dental use, since the compositions have got good appraisal such that the compositions can readily promote high polymerization degree on the surfaces of materials owing to the function of photo-polymerization and can also progress chemical polymerization even in depth where no sufficient light required for polymerization can reach.

However, camphorquinone itself has a color in vivid yellow, polymerizable compositions containing camphorquinone are colored yellow inappropriate for dental materials. Additionally, the vivid yellow of the polymerizable compositions containing camphorquinone fades through photo-irradiation, so that the color changes markedly between prior to and after polymerization. In recent years, the demand for aesthetic beauty from dental patients has been emphasized in the field of dental treatment, and it is said that the vivid yellow color and the color change between prior to and after polymerization are not suitable.

A combination of benzoyl peroxide, i.e. a polymerization initiator, and reducing agents such as tertiary amine, which has been used widely for chemically polymerizable compositions, is problematic in view of color stability in that the color of the cured products of such compositions readily changes when the products are exposed to hot water.

For the purpose of overcoming the problems, a dental composition containing acylphosphine oxide as a photo-polymerization initiator has been proposed (Japanese Patent Publication No. 6-55654). The cured products resulted from the photo-polymerizable compositions containing acylphosphine oxide as a photo-polymerization initiator are excellent in its color stability, but the photo-polymerizable compositions are disadvantageous in that polymerization is not sufficiently facilitated in depth because the curing depth of the composition is shallower than that of the polymerizable compositions containing camphorquinone.

A technique for improving the affinity between teeth and such cured products thereby increasing the adhesion strength between teeth and the cured products, by using an acidic monomer having an acid group together with a polymerizable unsaturated group for a part of polymerizable monomers to be used in dental materials, has been on the way of practical use. Though polymerizable compositions containing acidic monomers have such an advantage as stated above, the thickness of the resulting unpolymerized layer is so large that the hardness of the resulting cured product may be insufficient.

Because the burden over patients is less as the therapeutic treatment time is shorter, a dental material with such a high polymerization rate that can be cured for a short period has been expected.

Therefore, it is an object of the present invention to provide a polymerizable composition for dental use, the composition being colored suitable as a dental material, having less color change between prior to and after polymerization (prior to and after curing) and such a larger curing depth to produce cured products with sufficient hardness and strength even in depth.

Furthermore, it is the other object of the present invention to provide a polymerizable composition for dental use, in addition to the properties described above, being capable of producing cured products with such a small thickness of the unpolymerized layer on the surface and a higher hardness, having a larger polymerization rate so the composition can be cured for a short period of time, and having great adhesion to the teeth.

DISCLOSURE OF THE INVENTION

To attain the objects, the present inventors have made intensive investigations. Consequently, the inventors have found that the use of acylphosphine oxide as a photo-polymerization initiator, an organic peroxide as a chemical polymerization initiator, reducing agents such as the combination of tertiary amine and aromatic sulfinic acid and/or a salt thereof for a polymerizable composition containing a monomer with a polymerizable olefinic unsaturated group can impart excellent curability to the resulting polymerizable composition through any of photo-polymerization and chemical polymerization, which can further have suitable color for dental use, less color change between prior to and after polymerization (prior to and after curing) and great light resistance with less fading.

The present inventors have further found that cured products made from the polymerizable composition have a small thickness of the unpolymerized layer on the surface, a higher hardness; that the polymerizable composition has such large curing depth to produce cured products with sufficient hardness and strength even in depth; and that the composition has so excellent resistance to discoloration by hot water in darkness that the resulting cured products are hardly discolored even if the products are exposed to hot water in the oral cavity.

Still additionally, the present inventors have found that the polymerizable composition containing a monomer with an acid group together with a polymerizable olefinic unsaturated group, as a part of the polymerizable monomers in the composition, can more improve the adhesive strength to teeth while the resulting cured products can still retain the various excellent properties described above. The inventors have achieved the present invention on the basis of those findings.

It is not yet elucidated why the polymerizable composition according to the present invention can have such various excellent properties as described above, but it is speculated that an extremely great number of radicals are generated on the irradiated surface because of the higher quantum yield of acylphosphine oxide to be used as component (b) in the polymerizable composition, so that the polymerization heat and the radicals at such higher concentration on the surface may induce the decomposition of organic peroxides.

Thus, the present invention is a polymerizable composition for dental use, the composition comprising monomer (a) with a polymerizable olefinic unsaturated group, acylphosphine oxide (b), organic peroxide (c), tertiary amine (d) and aromatic sulfinic acid and/or a salt thereof(e).

In accordance with the present invention, additionally, the polymerizable composition for dental use, further containing a monomer with a polymerizable olefinic unsaturated group and an acid group for a part of the monomer (a), is encompassed within the preferable embodiments.

EMBODIMENT OF THE INVENTION

The monomer (a) to be used in the present invention may be any of monomers with a polymerizable olefinic unsaturated group. Among them, (meth)acrylate monomers are preferably used as the monomer (a), from the respect of the simplicity of the polymerization procedure and the safety for biological organisms.

The (meth)acrylate monomer to be used preferably in the present invention may be any of mono-functional (meth) acrylate monomers and polyfunctional (meth)acrylate monomers.

As such mono-functional (meth)acrylate monomers, use may preferably be made of esters of (meth)acrylic acid having alkyl groups with 1 to 12 carbon atoms and esters of (meth)acrylic acid containing aromatic groups with 6 to 12 carbon atoms, wherein the alkyl groups and aromatic groups composing the esters may contain substituents such as hydroxyl group and ether bonds.

Specific examples of the monofunctional (meth)acrylate monomers may include (meth)acrylates such as methyl (meth)acrylate, ethyl (meth)acrylate, n-butyl (meth)acrylate, iso-butyl (meth)acrylate, 2-ethylhexyl (meth)acrylate, lauryl (meth)acrylate, tridecyl (meth)acrylate, stearyl (meth) acrylate, cyclohexyl (meth)acrylate, benzyl (meth)acrylate, 2-hydroxyethyl (meth)acrylate, 2-hydroxypropyl (meth) acrylate, glycidyl (meth)acrylate, tetrahydrofurfuryl (meth) acrylate, allyl (meth)acrylate, 2-ethoxyethyl (meth)acrylate, methoxydiethylene glycol (meth)acrylate, methoxytetraethylene glycol (meth)acrylate, methoxypolyethylene glycol (meth)acrylate, phenoxy-diethyleneglycol (meth)acrylate, phenoxyhexaethyleneglycol (meth)acrylate, glycerol (meth) acrylate, tetrahydrofurfuryl (meth)acrylate, dicyclopentenyl (meth)acrylate, isobornyl (meth)acrylate, phenyl (meth) acrylate, pentaerythritol mono(meth)acrylate, dipentaerythritol mono(meth)acrylate, caprolactone modified tetrahydrofurfuryl (meth)acrylate, caprolactone modified dipentaerythritol (meth)acrylate, and caprolactone modified 2-hydroxyethyl (meth)acrylate.

Furthermore, preferable examples of the polyfunctional (meth)acrylate monomers may include di(meth)acrylates of alkylene glycol having 2 to 20 carbon atoms, di(meth) acrylates of the oligomers of said alkylene glycol, polyalkyleneglycol di(meth)acrylate, di(meth)acrylate derived from bisphenol A, (meth) acrylate monomers having three or more functional groups; and the examples additionally may include urethane (meth)acrylate esters as reaction products of 2 moles of (meth)acrylate having a hydroxyl group and one mole of diisocyanate (refer to for example polyfunctional urethane monomers disclosed in Japanese Patent Publication No. 55-33687 and Japanese Patent Application Laid-Open No. 56-152408).

More specifically, the polyfunctional (meth)acrylate may include for example ethylene glycol di(meth)acrylate, diethylene glycol di(meth)acrylate, triethylene glycol di(meth) acrylate, tetraethylene glycol di(meth)acrylate, polyethylene glycol di(meth)acrylate, 1,3-butylene glycol di(meth) acrylate, 1,6-hexane diol di(meth)acrylate, neopentyl glycol di(meth) acrylate, tripropylene glycol di(meth) acrylate, polypropylene glycol di(meth)acrylate, glycerol di(meth) acrylate, bisphenol A A di(meth)acrylate, bisphenol A glycidyl di(meth)acrylate, ethylene oxide modified bisphenol A di(meth)acrylate, ethylene oxide modified bisphenol A glycidyl di(meth)acrylate, 2,2-bis(4-methacryloxypropoxyphenyl) propane, 7,7,9-trimethyl-4, 13-dioxa-3,14-dioxo-5,12-diazahexadecane-1,16-diol di(meth)acrylate, neopentyl glycol hydroxypivalic acid ester di(meth)acrylate, caprolactone modified hydroxypivalic acid neopentyl glycol ester di(meth)acrylate, trimethylol ethane di(meth)acrylate, trimethylol propane di(meth) acrylate, trimethylol methane tri(meth)acrylate, trimethylol ethane tri(meth)acrylate, trimethylol propane tri(meth) acrylate, pentaerythritol tri(meth)acrylate, dipentaerythritol tri(meth)acrylate, pentaerythritol tetra(meth)acrylate, dipentaerythritol tetra(meth)acrylate, dipentaerythritol hexa (meth)acrylate, the reaction product of 3-chloro-2-hydroxypropyl (meth)acrylate and methylcyclohexane diisocyanate, the reaction product of 2-hydroxypropyl (meth)acrylate and methylcyclohexane diisocyanate, the reaction product of 2-hydroxypropyl (meth)acrylate and methylene bis (4-cyclohexylisocyanate), the reaction product of 2-hydroxypropyl(meth)acrylate and trimethylhexamethylene diisocyanate, the reaction product of 2-hydroxyethyl (meth)acrylate and isophorone diisocyanate, and the reaction product of 3-chloro-2-hydroxypropyl (meth)acrylate and isophorone diisocyanate.

The present polymerizable composition for dental use may contain one or more of the (meth)acrylate monomers described above. From the respect of the handling of the composition, curability and physical properties of the resulting cured products, the polymerizable composition for dental use preferably contains at least one of the monofunctional (meth)acrylate monomers and at least one of the polyfunctional (meth)acrylate monomers.

For using the present polymerizable composition for dental use as an adhesive and a bonding agent for dental use, furthermore, the composition preferably contains a strongly polar monomer having ability to promote the adhesion between teeth and metals, particularly a monomer with an acid group together with a polymerizable olefinic unsaturated group (referred to as "acid monomer" hereinbelow) for a part of the monomer (a).

When the present polymerizable composition for dental use contains the acid monomer, the content of the acid monomer is preferably 1 to 70% by weight, more preferably 5 to 50% by weight on the basis of the total weight of the monomer (a). The content of the acid monomer exceeding 70% by weight often causes deterioration of curing of the composition.

Examples of the acid group in the acid monomer may include the following groups of from phosphoric acid, diphosphate or derivatives thereof;

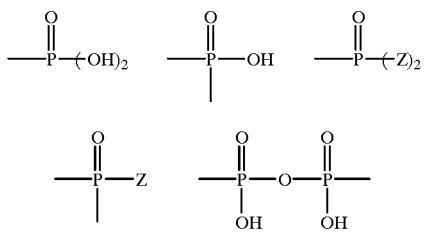

(wherein Z represents a halogen atom), carboxyl group (—COOH), carbohalide group (—COZ) (wherein Z represents a halogen atom), carboxylic anhydride group.

Specific examples of the acid monomer with the acid group may include what will be shown below.

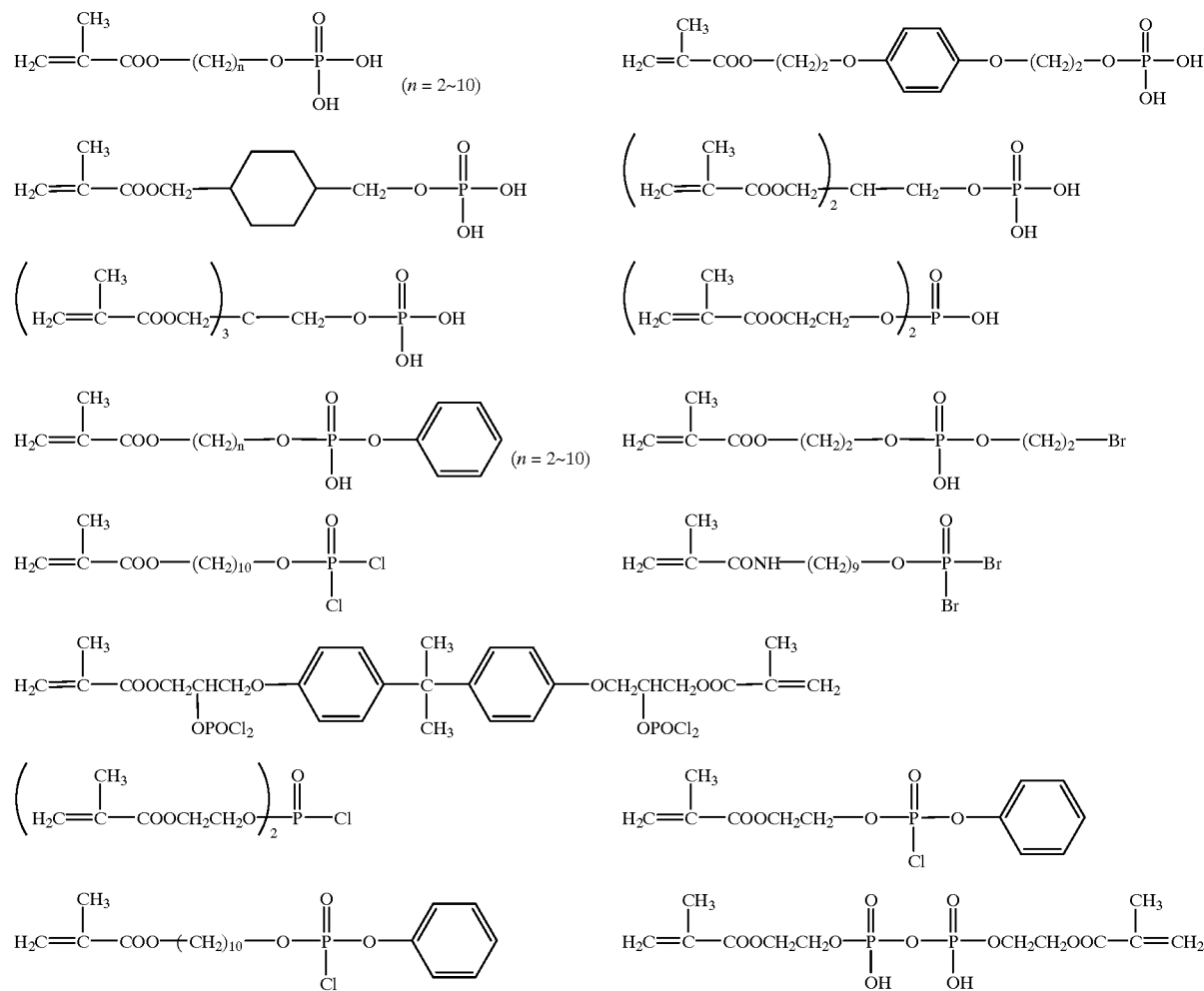

-continued

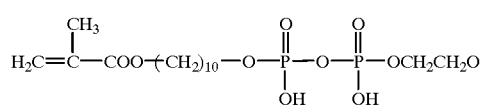

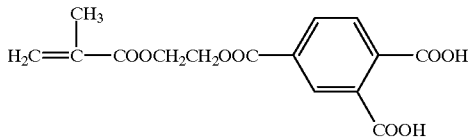

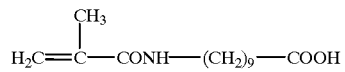

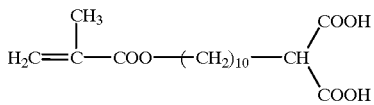

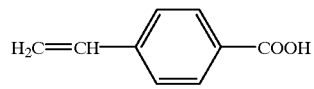

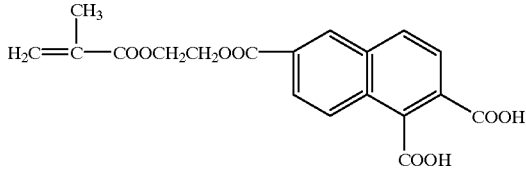

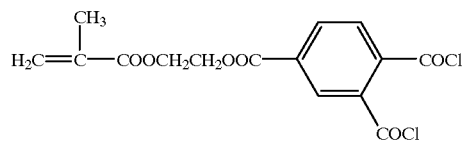

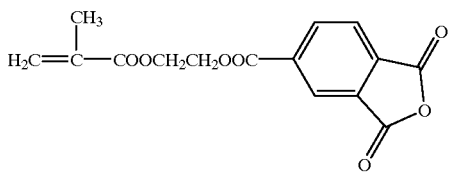

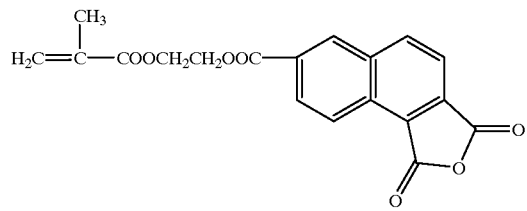

In accordance with the present invention, one or two or more of the acid monomers described above, for a part of the monomer (a), can be used in combination with one or two or more of the (meth)acrylates with no acid group.

The acylphosphine oxide (b) to be used in accordance with the present invention has a primary action as photopolymerization initiator, to initiate the polymerization of the monomer (a) in the polymerizable composition on photo-irradiation.

As the acylphosphine oxide (b) to be used in accordance with the present invention, use may be made of any acylphosphine oxide capable of initiating the polymerization of the monomer (a) on photo-irradiation, and specifically, use is preferably made of the acylphosphine oxide compound represented by the following general formula (I).

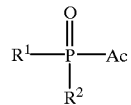
(I)

(wherein $R^1$ represents an alkyl group or an aryl group; $R^2$ represents an alkyl group, an aryl group or a group represented by the formula —$OR^3$ wherein $R^3$ represents an alkyl group or an aryl group; and Ac represents an acyl group.)

As the acylphosphine oxide (b) among them in accordance with the present invention, use is preferably made of benzoyldiphenylphosphine oxide within the general formula (I) wherein $R^1$ and $R^2$ are phenyl groups which may have or may not have substituent(s); and benzoylphenyl phosphinate ester wherein $R^1$ represents a phenyl group which may have or may not have substituent(s), $R^2$ represents a group represented by the formula —$OR^3$, and Ac represents a benzoyl group which may have or may not have substituent (s).

Specific examples of the benzoyldiphenylphosphine oxide and benzoylphenyl phosphinate ester to be preferably used in accordance with the present invention may include 2,4,6-trimethylbenzoyldiphenylphosphine oxide, 2,6-dimethylbenzoyldiphenylphosphine oxide, 2,6-dimethoxylbenzoyldiphenylphosphine oxide, 2,6-dichlorobenzoyldiphenylphosphine oxide, 2,3,5,6-tetramethylbenzoyldiphenylphosphine oxide, 2,4,6-trimethylbenzoylphenylphosphinic acid methyl ester, 2,4,6-trimethylbenzoylphenylphosphinic acid ethyl ester, and 2,4,6- trimethylbenzoylphenylphosphinic acid phenyl ester, and one or two or more of these compounds may be used.

As the acylphosphine oxide (b) among them in accordance with the present invention, use is particularly preferably made of 2,4,6-trimethylbenzoyldiphenylphosphine oxide represented by the following chemical formula (II) and/or 2,4,6-trimethylbenzoylphenylphosphinic acid alkyl ester represented by the chemical formula (III), from the respect of its stability.

(II)

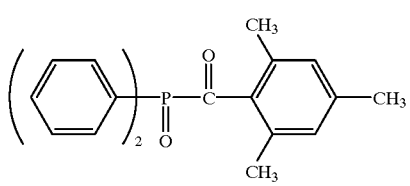

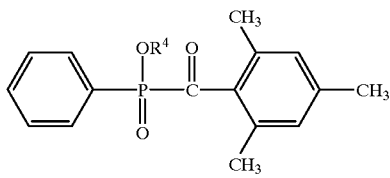

(III)

(wherein R⁴ represents an alkyl group with one to 4 carbon atoms.)

The content of the acylphosphine oxide (b) in the polymerizable composition is preferably 0.05 to 20% by weight, more preferably 0.1 to 10% by weight on the basis of the weight of the monomer (a), in view of the adjustment of the photo-sensitivity of the polymerizable composition.

The organic peroxide (c) to be used in accordance with the present invention may be any organic peroxide capable of initiating the polymerization of the monomer (a) through thermal or redox reaction, specifically including diacyl peroxides, peroxyesters, dialkyl peroxides, peroxyketals, ketone peroxides, and hydroperoxides. Specific examples of the diacyl peroxides may include benzoyl peroxide, 2,4-dichlorobenzoyl peroxide, and m-toluoyl peroxide. Specific examples of the peroxyesters may include t-butylperoxybenzoate, bis-t-butylperoxyisophthalate, 2,5-dimethyl-2,5-bis(benzoylperoxy)hexane, t-butylperoxy-2-ethylhexanoate, and t-butylperoxyisopropylcarbonate. Specific examples of the dialkyl peroxides may include dicumyl peroxide, di-t-butyl peroxide, and lauroyl peroxide. Additionally, specific examples of the peroxyketals may include 1,1-bis(t-butylperoxy)3,3,5-trimethylcyclohexane. And specific examples of the ketone peroxides may include methyl ethyl ketone peroxide. Then, specific examples of the hydroperoxides may include t-butyl hydroperoxide. One or two or more of these organic peroxides may be used satisfactorily.

So as to impart a proper polymerization rate to the polymerizable composition for dental use, the content of the organic peroxide (C) in the polymerizable composition in accordance with the present invention is preferably 0.05 to 20% by weight, more preferably 0.1 to 10% by weight on the basis of the weight of the monomer (a).

The tertiary amine (d) to be used in accordance with the present invention primarily functions as a reducing agent. As the tertiary amine (d), any tertiary amine is satisfactory as long as it functions as a reducing agent in combination with an aromatic sulfinic acid or a salt thereof in the presence of the acylphosphine oxide (b) and the organic peroxide (c). They include aromatic tertiary amine and/or aliphatic tertiary amine. Specific examples of the aromatic tertiary amine may include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-bis(2-hydroxyethyl)-3,5-di i-propylaniline, N,N-bis(2-hydroxyethyl)-3,5-di t-butylaniline, 4-dimethylaminobenzoate ethyl, 4-dimethylaminobenzoate n-butoxyethyl, and 4-dimethylaminobenzoate (2-methacryloyloxy)ethyl.

Furthermore, specific examples of the aliphatic tertiary amine (d) may include trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

In accordance with the present invention, one or two or more of these tertiary amines may be used.

From the respect of imparting a proper polymerization rate and suppressing discoloration, the content of the tertiary amine (d) in the polymerizable composition for dental use in accordance with the present invention is preferably 0.05 to 10% by weight, more preferably 0.1 to 5% by weight on the basis of the weight of the monomer (a).

The aromatic sulfinic acid or a salt thereof (e) (referred to as "aromatic sulfinic acid (salt) (e)") to be used in accordance with the present invention primarily functions as a reducing agent. As the aromatic sulfinic acid (salt) (e), any aromatic sulfinic acid (salt) (e) is satisfactory as long as it functions as a reducing agent in combination with the tertiary amine (d) in the presence of the acylphosphine oxide (b) and the organic peroxide (c). Specific examples thereof include benzenesulfinic acid, sodium benzenesulfinate, potassiumbenzenesulfinate, calciumbenzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, 2,4,6-trimethylsodium benzenesulfinate, 2,4,6-trimethylbenzenesulfinate potassium, 2,4,6-trimethylbenzenesulfinate calcium, 2,4,6-trimethylbenzenesulfinate lithium, 2,4,6-triethylbenzenesulfinic acid, 2,4, 6-triethylsodium benzenesulfinate 2,4,6-triethylbenzenesulfinate potassium, 2,4,6-triethylbenzenesulfinate calcium, 2,4,6-i-propylbenzenesulfinic acid, 2,4,6-i-propylsodium benzenesulfinate , 2,4,6-i-propylbenzenesulfinate potassium, and 2,4,6-I-propylbenzenesulfinate calcium. For the polymerizable composition for dental use in accordance with the present invention, one or two or more of these aromatic sulfinic acids (salts) may be used.

From the respect of imparting a proper polymerization rate, the content of the aromatic sulfinic acid (salt) (e) in the polymerizable composition for dental use in accordance with the present invention is preferably 0.05 to 10% by weight, more preferably 0.1 to 5% by weight on the basis of the weight of the monomer (a).

In combination with the monomer (a), the polymerizable composition for dental use in accordance with the present invention essentially contains the acylphosphine oxide (b), the organic peroxide (c), the tertiary amine (d) and the aromatic sulfinic acid (salt) (e).

When the polymerization composition for dental use containing camphorquinone instead of acylphosphine oxide (b), the thickness of the unpolymerized layer on the surface of the resulting cured product from the composition is large, whereby the hardness thereof is decreased, as well as causing the reduction of the light resistance of the cured product, thereby leading to the increase of the color change between prior to and after polymerization. When the polymerizable composition for dental use does not contain the tertiary amine (d), alternatively, the curing depth of the composition is less. When the polymerizable composition for dental use does not contain the aromatic sulfinic acid (salt) (e), furthermore, the thickness of unpolymerized layer on the surface of theresulting cured product is large, whereby the hardness thereof is decreased, as well as causing the reduction of the light resistance of the cured product, thereby leading to the enhancement of the color change between prior to and after polymerization.

From the respect of the stability of the composition, during storage and before use of the composition, the polymerizable composition for dental use in accordance with the present invention should be prepared in multi-package, wherein the organic peroxide (c) is separated from the tertiary amine (d) and the aromatic sulfinic acid (salt) (e). The multi-packing includes (i) two packages comprising the first package containing the monomer (a), the acylphosphine oxide (b) and the organic peroxide (c) and the second package containing the tertiary amine (d) and the aromatic sulfinic acid (salt) (e); (ii) two packages comprising the first package containing a part of the monomer (a), the acylphosphine oxide (b) and the organic peroxide (c) and the second package containing the remaining part of the monomer (a), the tertiary mine (d) and the aromatic sulfinic acid (salt) (e); (iii) two packages comprising the first package containing the monomer (a) and the organic peroxide (c) and the second package containing the acylphosphine oxide (b), the tertiary amine (d) and the aromatic sulfinic acid (salt) (e); (iv) three packages comprising the first package containing a part of the monomer (a), the acylphosphine oxide (b) and the organic peroxide (c), the second package containing the remaining part of the monomer (a) and the tertiary mine (d), and the third package containing the remaining part of the monomer (a) and the aromatic sulfinic acid (salt)(e).

The polymerizable composition for dental use in accordance with the present invention may satisfactorily contain a filler, if necessary, in combination with the components described above. Particularly when the polymerizable composition for dental use in accordance with the present invention is used for a bonding agent or a composite resin for dental use, the composition preferably contains a filler, from the respect of the strength of the resulting cured product.

The content of a filler in the polymerizable composition for dental use is preferably at a ratio of the monomer (a): =the filler=100:0 to 10:90 (in weight ratio). Particularly when the polymerizable composition for dental use in accordance with the present invention is a bonding agent or a composite Iresin, the composition preferably contains a filler within a ratio of the monomer (a):the filler=80:20 to 10:90 (in weight ratio); when the polymerizable composition is an adhesive agent, the composition preferably contains a filler within a ratio of the monomer (a):the filler=70:30 to 100:0 (in weight ratio).

The filler may satisfactorily be any of inorganic fillers, organic fillers, inorganic and organic complex fillers, or a mixture of inorganic fillers and organic fillers.

Examples of such inorganic fillers may include soda glass, lithium borosilicate glass, barium glass, strontium glass, zinc glass, fluoroaluminum borosilicate glass, borosilicate glass, crystal quartz, fumed silica, synthetic silica, alumina silicate, amorphous silica, glass ceramics or mixtures thereof.

From the respect of uniformity for mixing, generally, the particle size of the inorganic fillers is preferably 150 $\mu$m or less, more preferably 100 $\mu$m or less, but inorganic fillers outside above limitation may also be used. If necessary, several types of inorganic fillers with different particle sizes may be mixed together and the resulting mixture may satisfactorily be used.

So as to improve the affinity with the monomer (a) and with the resulting cured product after polymerization, preferably, the inorganic fillers may be subjected to surface treatment. As such surface treating agent, use may satisfactorily be made of conventionally known silane compounds (silane coupling m-,z agents), specifically including for example vinyltrimethoxysilane, vinyltriethoxysilane, vinyltrichlorosilane, vinyltri($\beta$-methoxyethoxy)silane, $\gamma$-methacryloxypropyltrimethoxysilane, $\gamma$-glycidoxypropyltrimethoxysilane, $\gamma$-mercaptopropyltrimethoxysilane, and $\gamma$-aminopropyltriethoxysilane.

The organic fillers may include organic polymer powder which is preliminarily produced by polymerizing the monomer (a).

Additionally, use may satisfactorily be made of composite fillers recovered by polymerizing a polymerizable monomer in the presence of an inorganic filler in dispersion.

The present polymerizable composition for dental use may contain fluoride releasing fillers, for example polysiloxane coated metal fluorides as described in Japanese Patent Application Laid-Open No. 10-36116, and in that case, a polymerizable composition for dental use with an effect of preventing caries can be obtained.

The present photo-polymerizable composition for dental use may contain polymerization inhibitors, ultraviolet absorbents, pigments, and solvents. Specific examples of the solvents may include water, ethanol, i-propanol, acetone, dimethylsulfoxide, dimethylformamide, ethyl acetate, butyl acetate, and one or two or more of these solvents may be used.

The polymerizable composition of the present invention can effectively be used for utilities, for example as cements for dental use, such as resin cement and resin reinforced glass ionomer cement, composite resins for dental use and compomers for dental use, such as filling and restorative materials, core build-up materials, pits and fissure sealant; adhesives for dental use, such as bonding agents and adhesives for orthodontic devices; dental primers; opaque primers and the like.

For using the present polymerizable composition for dental use as a composite resin, even a deep cavity can be filled, owing to the large curing depth, so that a cured product with greater hardness is yielded even in such depth, effectively retaining aesthetic beauty with less discoloration.

When the present polymerizable composition for dental use is used as a cement, the composition has such greater surface curability that the wear of cement lines can be prevented, with less discoloration, which effectively works to retain aesthetic beauty.

When the present polymerizable composition for dental use is used as a bonding agent, the composition has such a larger polymerization rate that the adhesion procedure is simple, which works to readily promote treatment procedures by using other restorative materials such as composite resin.

When the present polymerizable composition for dental use is used as primer, the composition has such excellent curability of penetrated components into the tooth that the adhesion can be improved.

Additionally, the polymerizable composition of the present invention may satisfactorily be used as coating agents, adhesives and filling materials for general industries, besides dental uses.

BEST MODE FOR CARRYING OUT THE INVENTION

The present invention will now be described in detail in the following examples, but it is in no way intended to be limited by these examples.

In the following examples, the properties of the polymerizable composition or the cured product thereof after polymerization were measured as follows.

(1) Thickness of Surface Unpolymerized Layer

In the following examples and comparative examples, the compositions A and B were equally weighed and mixed together, to prepare individual polymerizable compositions for dental use, which were then filled in a mold made of Teflon having a diameter of 10 mm and a thickness of 1 mm, followed by smoothing of the surface and subsequent irradiation with a dental irradiator (manufactured by Morita Corporation; "Lightel II") for 20 seconds. After irradiation, the unpolymerized part on the surface was wiped off, and then, the thickness of the unpolymerized layer was calculated on the basis of the change in weight between prior to and after the wiping procedure.

(2) Brinell Hardness

In the following examples and comparative examples, the compositions A and B were equally weighed and mixed together, to prepare individual polymerizable compositions for dental use, which were then filled in a metal mold of a diameter of 10 mm and a thickness of 5 mm, followed by covering under pressure with a glass plate, and the compositions were left to stand in darkness at 37° C. for 30 minutes, to prepare products cured through chemical polymerization. The Brinell hardness of the surface of each cured product was measured, after taking the glass plate off, by using Microbrinell Hardness Tester (manufactured by Mori Tester Seisakusho).

(3) Curing Depth

In the following examples and comparative examples, the compositions A and B were equally weighed and mixed together, to prepare individual polymerizable compositions for dental use, which were then filled in a metal mold of a diameter of 4 mm and a height of 12 mm, followed by covering with cover glass, and then, the compositions were irradiated from the above with a dental irradiator (manufactured by Morita Corporation; "Lightel II") for 20 seconds. Immediately after irradiation, the cured products were removed out of the mold, to wipe off the unpolymerized layer and measured the height of the cured products with a slide gauge.

(4) Light Resistance ($\Delta E_1$)

In the following examples and comparative examples, the compositions A and B were equally weighed and mixed together, to prepare individual polymerizable compositions for dental use, which were then filled in a metal mold of a diameter of 20 mm and a thickness of 1 mm, followed by photo-irradiation with a dental irradiator (manufactured by Morita Tokyo Corporation; "α-Light II") for 5 minutes to cure the composition. A half surface of each of the cured product was covered with aluminium foil, followed by irradiation of light of 150,000 lux in water at 37° C. for 24 hours. By using a color measuring system (manufactured by Nippon Denshoku; "Σ90"), the colors of the resulting non-irradiated face covered by aluminium foil and the resulting irradiated face were counted on an L*a*b* color specification system. Then, the color difference between above-mentioned two faces was determined by the following equation; $\Delta E_1 = (\Delta L^{*2} + \Delta a^{*2} + \Delta b^{*2})^{1/2}$, which was used as an indicator of light resistance.

(5) Color Change Between Prior to and After Polymerization ($\Delta E_2$)

In the following examples and comparative examples, the compositions A and B were equally weighed and mixed together, to prepare individual polymerizable compositions for dental use, which were then filled in a metal mold of a diameter of 20 mm and a thickness of 1 mm, to count the colors on an L*a*b* color specification system by using a color measuring system (manufactured by Nippon Denshoku; "Σ90"). Then, the compositions were irradiated with a dental irradiator (manufactured by Morita Tokyo Corporation; "α-Light III") for 5 minutes, and the colors of the resulting cured products were counted in the same manner, to determine the color change between prior to and after polymerization by the following equation $$\Delta E_2 = (\Delta L^{*2} + \Delta a^{*2} + \Delta b^{*2})^{1/2}.$$

(6) Color Fastness in Hot Water and in Darkness ($\Delta E_3$)

In the following examples and comparative examples, the compositions A and B were equally weighed and mixed together, to prepare individual polymerizable compositions for dental use, which were then filled in a metal mold of a diameter of 20 mm and a thickness of 1 mm and were then left to stand in darkness at 37° C. for 30 minutes, to prepare cured products. By using a color difference meter (manufactured by Nippon Denshoku; "Σ90"), the color of the resulting cured products was counted on an L*a*b* color specification system. Then, the cured products were placed in hot water (purified water) at 70° C. in darkness for one week. After drawing out the products from the water, the color was counted in a similar manner, to determine the color change between prior to and after immersion in hot water, by the following equation $\Delta E_3 = (\Delta L^{*2} + \Delta a^{*2} + \Delta b^{*2})^{1/2}$.

(7) Photo-polymerization Time

In the following examples and comparative examples, the compositions A and B were equally weighed and mixed together, and the tip of a thermocouple was immediately inserted into the resulting mixtures (polymerizable compositions), followed by photo-irradiation with a dental irradiator (manufactured by Morita Corporation; "Lightel II"). The time required for the temperature of the polymerization heat to reach the peak, monitoring with the thermocouple, was designated as photo-polymerization time.

EXAMPLES 1 to 3 AND COMPARATIVE EXAMPLES 1 AND 2

(i) By using bisphenol A A diglycidyl ether (abbreviated as "Bis-GMA" hereinafter), triethylene glycol dimethacrylate (abbreviated as "TEGDMA" hereinafter), 10-methacryloyloxy-decyldihydrogen phosphate (abbreviated as "MDP" hereinafter) and 2-hydroxyethyl methacrylate (abbreviated as "HEMA" hereinafter) as the monomer (a), and by using 2,4,6-trimethylbenzoyldiphenylphosphine oxide or 2,4,6-trimethylbenzoylphenylphosphinate ethyl ester as the acylphosphine oxide (b), benzoyl peroxide as the organic peroxide (c) and N,N-bis(2-hydroxyethyl)-p-toluidine (abbreviated as "diethanol-p-toluidine" hereinafter) as the tertiary amine (d), and sodium benzenesulfinate as the aromatic sulfinic acid (salt) (e), in combination with camphorquinone, quartz powder and polysiloxane coated sodium fluoride, all the above substances being at the amounts shown in Table 1 below, two polymerizable compositions for dental use, the composition A and the composition B, were prepared respectively.

(ii) By using the polymerizable compositions for dental use as prepared above in (i), the thickness of the unpolymerized layer on the surface, Brinell hardness and light resistance of the cured products from the polymerizable compositions were measured according to the methods described above. The results are as shown in Table 1 below.

TABLE 1

|  | Example 1 | Example 2 | Example 3 | Comparative Example 1 | Comparative Example 2 |
|---|---|---|---|---|---|
| [Polymerizable compositions for dental use] Composition A (parts by weight): Monomer (a)[1] |  |  |  |  |  |
| Bis-GMA | 40 | 40 | 40 | 40 | 40 |
| TEGDMA | 40 | 40 | 40 | 40 | 40 |
| MDP | 20 | 20 | 20 | 20 | 20 |
| Component (b)[2] |  |  |  |  |  |
| $b_1$ | 2 | 0 | 2 | 0 | 2 |
| $b_2$ | 0 | 2 | 0 | 0 | 0 |
| Component (c) |  |  |  |  |  |
| Benzoyl peroxide | 2 | 2 | 2 | 2 | 2 |
| Camphorquinone | 0 | 0 | 0 | 2 | 0 |
| Quartz powder | 300 | 300 | 300 | 300 | 300 |
| Composition B (parts by weight): Monomer (a)[1] |  |  |  |  |  |
| Bis-GMA | 20 | 20 | 20 | 20 | 20 |
| TEGDMA | 30 | 30 | 30 | 30 | 30 |
| HAMA | 50 | 50 | 50 | 50 | 50 |
| Component (d) |  |  |  |  |  |
| Diethanol-p-toluidine | 1 | 1 | 1 | 1 | 1 |
| Component (e) |  |  |  |  |  |
| Sodium benzenesulfinate | 1 | 1 | 1 | 1 | 0 |
| Polysiloxane coated sodium fluoride | 0 | 0 | 30 | 0 | 0 |
| Quartz powder | 300 | 300 | 270 | 300 | 300 |
| [Properties] |  |  |  |  |  |
| Thickness of unpolymerized layer (μm) | 21.3 | 23.5 | 22.8 | 34.7 | 47.3 |
| Brinell hardness (HB) | 41.5 | 39.6 | 42.1 | 38.9 | 21.3 |
| Light resistance ($\Delta E_1$) | 5.56 | 4.98 | 5.23 | 9.96 | 9.92 |

[1]Monomer (a)
Bis-GMA: bisphenol A diglycidyldimethacrylate
TEGDMA: triethyleneglycol dimethacrylate
MDP: 10-methacryloyloxydecyldihydrogen phosphate
HEMA: 2-hydroxyethyl methacrylate
[2]Component (b) [acylphosphine oxide]
$b_1$: 2,4,6-trimethylbenzoyldiphenylphosphine oxide
$b_2$: 2,4,6-trimethylbenzoylphenylphosphinate ethyl ester The results in Table 1 above indicate that the polymerizable compositions containing the monomer (a), the acylphosphine oxide (b), the organic peroxide (c), the tertiary amine (d) and the aromatic sulfinic acid (salt) (e) for dental use in Examples 1 to 3 have excellent surface curability because of the small thickness of the unpolymerized layers on the surface, high Brinell hardness and excellent chemical curability, and smaller values of $\Delta E_1$ showing superior light resistance.

The polymerizable composition with no acylphosphine oxide (b) contained therein for dental use in Comparative Example 1 has a larger thickness of the unpolymerized layer on the surface than those in Examples 1 to 3, indicating far poorer surface curability, and has larger values of $\Delta E_1$ than those in Examples 1 to 3, indicating poor light resistance.

The polymerizable composition with no tertiary amine (d) contained therein for dental use in Comparative Example 2 has a far larger thickness of the unpolymerized layer on the surface than those in Examples 1 to 3, indicating poorer surface curability, and has far lower Brinell hardness than those of Examples 1 to 3, showing poorer chemical curability, and larger values of $\Delta E_1$ than those in Examples 1 to 3, showing poor light resistance.

EXAMPLES 4 to 6 AND COMPARATIVE EXAMPLES 3 to 4

(i) By using bisphenol A diglycidyl ether (Bis-GMA) and triethyleneglycol dimethacrylate (TEGDMA) as the monomer (a) and by using 2,4,6-trimethylbenzoyldiphenylphosphine oxide or 2,4,6-trimethylbenzoylphenylphosphinate ethyl ester as the acylphosphine oxide (b), benzoyl peroxide as the organic peroxide (c) and diethanol-p-toluidine or 4-dimethylaminobenzoate ethyl as the tertiary amine (d), and sodium benzenesulfinate as the aromatic sulfinic acid (salt) (e), in combination with camphorquinone, quartz powder and barium glass, all the above substances being at the ratios shown in Table 2 below, two polymerizable compositions for dental use, comprising the composition A and the composition B, were individually prepared as shown in the following Table 2.

(ii) By using the polymerizable compositions for dental use as prepared above in (i), the curing depth and the color difference ($\Delta E_2$) between prior to and after polymerization were measured according to the methods described above. The results are as shown in Table 2 below.

TABLE 2

|  | Example 4 | Example 5 | Example 6 | Comparative Example 3 | Comparative Example 4 |
|---|---|---|---|---|---|
| [Polymerizable compositions for dental use] Composition A (parts by weight): Monomer (a)[1] |  |  |  |  |  |
| Bis-GMA | 70 | 70 | 70 | 70 | 70 |
| TEGDMA | 30 | 30 | 30 | 30 | 30 |
| Component (b)[2] |  |  |  |  |  |
| $b_1$ | 1 | 0 | 1 | 0 | 1 |
| $b_2$ | 0 | 1 | 0 | 0 | 0 |
| Component (c) |  |  |  |  |  |
| Benzoyl peroxide | 2 | 2 | 2 | 2 | 2 |
| Camphorquinone | 0 | 0 | 0 | 1 | 0 |
| Barium glass | 400 | 400 | 400 | 400 | 400 |
| Composition B (parts by weight): Monomer (a)[1] |  |  |  |  |  |
| Bis-GMA | 70 | 70 | 70 | 70 | 70 |
| TEGDMA | 30 | 30 | 30 | 30 | 30 |
| Component (d) |  |  |  |  |  |
| Diethanol-p-toluidine | 2 | 2 | 0 | 2 | 0 |
| 4-dimethylaminobenzoate ethyl | 0 | 0 | 2 | 0 | 0 |
| Component (e) |  |  |  |  |  |
| Sodium benzenesulfinate | 2 | 2 | 2 | 2 | 2 |
| Quartz powder | 350 | 350 | 350 | 350 | 350 |
| [Properties] |  |  |  |  |  |
| Curing depth (mm) | 4.86 | 4.66 | 5.16 | 4.52 | 3.28 |

TABLE 2-continued

|  | Example 4 | Example 5 | Example 6 | Comparative Example 3 | Comparative Example 4 |
|---|---|---|---|---|---|
| Color difference between prior to and after polymerization ($\Delta E_2$) | 5.55 | 5.22 | 5.64 | 8.64 | 5.81 |

[1] Monomer (a)
Bis-GMA: bisphenol A diglycidyl dimethacrylate
TEGDMA: triethyleneglycol dimethacrylate
[2] Component (b) [acylphosphine oxide]
$b_1$: 2,4,6-trimethylbenzoyldiphenylphosphine oxide
$b_2$: 2,4,6-trimethylbenzoylphenylphosphinate ethyl ester The results in Table 2 above indicate that the polymerizable compositions containing the monomer (a), the acylphosphine oxide (b), the organic peroxide (c), the tertiary amine (d) and the aromatic sulfinic acid (salt) (e) for dental use in Examples 4 to 6 have larger curing depth with higher photo-polymerization, and smaller values of color difference ($\Delta E_2$) between prior to and after polymerization, suggesting excellent color.

Alternatively, the polymerizable composition containing camphorquinone in place of the acylphosphine oxide (b) in Comparative Example 3 has a smaller curing depth than those in Examples 4 to 6, indicating poorer photo-polymerization, and larger values of color difference ($\Delta E_2$) between prior to and after polymerization, showing that the color of the composition largely changes between prior to and after polymerization.

The polymerizable composition with no tertiary amine (d) contained therein for dental use in Comparative Example 4 has far smaller curing depth than those in Examples 4 to 6, indicating far poorer photo-polymerization than those of Examples 4 to 6, and larger values of color difference ($\Delta E_2$) between prior to and after polymerization, showing larger color change between prior to and after polymerization.

EXAMPLES 7 AND 8 AND COMPARATIVE EXAMPLE 5

(i) By using bisphenol A diglycidyl ether (Bis-GMA), triethyleneglycol dimethacrylate (TEGDMA), 10-methacryloyloxydecyldihydrogen phosphate (MDP) and 2-hydroxyethyl methacrylate (HEMA) as the monomer (a), and by using 2,4,6-trimethylbenzoyldiphenylphosphine oxide or 2,4,6-trimethylbenzoylphenylphosphinate ethyl ester as the acylphosphine oxide (b), benzoyl peroxide as the organic peroxide (c) and diethanol-p-toluidine as the tertiary amine (d), and sodium benzenesulfinate as the aromatic sulfinic acid (salt) (e), in combination with camphorquinone and colloidal silica, all the above substances being at the amounts shown in Table 3 below, two polymerizable compositions for dental use, comprising the composition A and the composition B as shown in Table 3 were individually prepared.

(ii) By using the polymerizable compositions for dental use as prepared above in (i), the photo-polymerization time was measured according to the method described above. The results are as shown in Table 3 below.

TABLE 3

|  | Example 7 | Example 8 | Comparative Example 5 |
|---|---|---|---|
| [Polymerizable compositions for dental use] | | | |
| Composition A (parts by weight): | | | |
| Monomer (a)[1] | | | |
| Bis-GMA | 50 | 50 | 50 |
| TEGDMA | 40 | 40 | 40 |
| MPD | 10 | 10 | 10 |
| Component (b)[2] | | | |
| $b_1$ | 3 | 0 | 0 |
| $b_2$ | 0 | 3 | 0 |
| Component (c) | | | |
| Benzoyl peroxide | 2 | 2 | 2 |
| Camphorquinone | 0 | 0 | 3 |
| Colloidal silica | 10 | 10 | 10 |
| Composition B (parts by weight): | | | |
| Monomer (a)[1] | | | |
| Bis-GMA | 30 | 30 | 30 |
| TEGDMA | 40 | 40 | 40 |
| HEMA | 30 | 30 | 30 |
| Component (d) | | | |
| Diethanol-p-toluidine | 2 | 2 | 2 |
| Component (e) | | | |
| Sodium benzenesulfinate | 2 | 2 | 2 |
| [properties] | | | |
| Photo-polymerization time (seconds) | 8 | 9 | 13 |

[1] Monomer (a)
Bis-GMA: bisphenol A diglycidyl dimethacrylate
TEGDMA: triethyleneglycol dimethacrylate
MDP: 10-methacryloyloxydecyldihydrogen phosphate
HEMA: 2-hydroxyethyl methacrylate
[2] Component (b) [acylphosphine oxide]
$b_1$: 2,4,6-trimethylbenzoyldiphenylphosphine oxide
$b_2$: 2,4,6-trimethylbenzoylphenylphosphinate ethyl ester The results in Table 3 above indicate that the polymerizable compositions containing the monomer (a), the acylphosphine oxide (b) i.e. 2,4,6-trimethylbenzoyldiphenylphosphine oxide or 2,4,6-trimethylbenzoylphenylphosphinate ethyl ester, the organic peroxide (c) i.e. benzoyl peroxide, the tertiary amine (d) i.e. diethanol-p-toluidine and the aromatic sulfinic acid (salt) (e) i.e. sodium benzenesulfinate for dental use in Examples 7 and 8 have a short photo-polymerization time, suggesting that the compositions can be polymerized and cured on photo-irradiation for a short time.

The polymerizable composition for dental use, containing camphorquinone instead of the acylphosphine oxide (b), in Comparative Example 5, has a longer photo-polymerization time than those in Examples 7 and 8, indicating that a longer time is required for polymerizing and curing the composition on photo-irradiation.

EXAMPLES 9 AND 10 AND COMPARATIVE EXAMPLE 6

(i) By using bisphenol A A diglycidyl ether (Bis-GMA) and triethyleneglycol dimethacrylate (TEGDMA) as the monomer (a), 2,4,6-trimethylbenzoyldiphenylphosphine oxide or 2,4,6-trimethylbenzoylphenylphosphinate ethyl ester as the acylphosphine oxide (b), benzoyl peroxide as the organic peroxide (c) and diethanol-p-toluidine as the tertiary amine (d), and sodium benzenesulfinate as the aromatic sulfinic acid (salt) (e), in combination with camphorquinone and quartz powder, all the above substances being at the ratios shown in Table 4 below, two polymerizable compositions for dental use, comprising the composition A and the composition B as shown in Table 4 were individually prepared.

(ii) By using the polymerizable compositions for dental use as prepared above in (i), the Brinell hardness and curing depth were measured according to the methods described above. The results are as shown in Table 4 below.

TABLE 4

|  | Example 9 | Example 10 | Comparative Example 6 |
|---|---|---|---|
| [Polymerizable compositions for dental use] Composition A (parts by weight): Monomer (a)[1] |  |  |  |
| Bis-GMA | 70 | 70 | 70 |
| TEGDMA | 30 | 30 | 30 |
| Component (b)[2] |  |  |  |
| b$_1$ | 1 | 0 | 1 |
| b$_2$ | 0 | 1 | 0 |
| Component (d) |  |  |  |
| Diethanol-p-toluidine | 0.5 | 0.5 | 0 |
| Component (e) |  |  |  |
| Sodium benzenesulfinate | 0.5 | 0.5 | 0.5 |
| Quartz powder | 400 | 400 | 400 |
| Composition B (parts by weight): Monomer (a)[1] |  |  |  |
| Bis-GMA | 70 | 70 | 70 |
| TEGDMA | 30 | 30 | 30 |
| Component (c) |  |  |  |
| Benzoyl peroxide | 2.5 | 2.5 | 2.5 |
| Quartz powder | 400 | 400 | 400 |
| [Properties] |  |  |  |
| Brinell hardness (HB) | 80.6 | 81.6 | 73.5 |
| Curing depth (mm) | 6.53 | 6.47 | 4.85 |

[1]Monomer (a)
Bis-GMA: bisphenol A diglycidyl dimethacrylate
TEGDMA: triethyleneglycol dimethacrylate
[2]Component (b) [acylphosphine oxide]
b$_1$: 2,4,6-trimethylbenzoyldiphenylphosphine oxide
b$_2$: 2,4,6-trimethylbenzoylphenylphosphinate ethyl ester The results above in Table 4 indicate that the polymerizable compositions containing the monomer (a), the acylphosphine oxide (b), the organic peroxide (c), the tertiary amine (d) and the aromatic sulfinic acid (salt) (e) for dental use in Examples 9 and 10 have greater Brinell hardness and excellent chemical polymerization as well as larger curing depth, than those of the polymerizable composition for dental use in Comparative Example 6, suggesting excellent photo-polymerization.

EXAMPLES 11 AND 12 AND COMPARATIVE EXAMPLE 7

(i) By using bisphenol A diglycidyl ether (Bis-GMA) and triethyleneglycol dimethacrylate (TEGDMA) as the monomer (a), and by using 2,4,6-trimethylbenzoyldiphenylphosphine oxide or 2,4,6-trimethylbenzoylphenylphosphinate ethyl ester as the acylphosphine oxide (b), benzoyl peroxide as the organic peroxide (c) and diethanol-p-toluidine as the tertiary amine (d), and sodium benzenesulfinate as the aromatic sulfinic acid (salt) (e), in combination with camphorquinone, all the above substances being at the ratios shown in Table 5 below, two polymerizable compositions for dental use, comprising the composition A and the composition B as shown in Table 5 were individually prepared.

(ii) By using the polymerizable compositions for dental use as prepared above in (i), the light resistance ($\Delta E_1$), the color change ($\Delta E_2$) between prior to and after polymerization and the color fastness in hot water and in darkness ($\Delta E_3$) were measured. The results are as shown in Table 5 below.

TABLE 5

|  | Example 11 | Example 12 | Comparative Example 7 |
|---|---|---|---|
| [Polymerizable compositions for dental use] Composition A (parts by weight): Monomer (a)[1] |  |  |  |
| Bis-GMA | 70 | 70 | 70 |
| TEGDMA | 30 | 30 | 30 |
| Component (b)[2] |  |  |  |
| b$_1$ | 1 | 0 | 0 |
| b$_2$ | 0 | 1 | 0 |
| Component (d) |  |  |  |
| Diethanol-p-toluidine | 0.5 | 0.5 | 0.5 |
| Component (e) |  |  |  |
| Sodium benzenesulfinate | 0.5 | 0.5 | 0.5 |
| Camphorquinone | 0 | 0 | 1 |
| Composition B (parts by weight): Monomer (a)[1] |  |  |  |
| Bis-GMA | 70 | 70 | 70 |
| TEGDMA | 30 | 30 | 30 |
| Component (c) |  |  |  |
| Benzoyl peroxide | 1 | 1 | 1 |
| [Properties] |  |  |  |
| Light resistance ($\Delta E_1$) | 1.39 | 1.28 | 4.27 |
| Color change between prior to and after polymerization ($\Delta E_2$) | 1.26 | 1.28 | 3.65 |
| Color fastness in hot water and in darkness ($\Delta E_3$) | 5.43 | 4.97 | 6.23 |

[1]Monomer (a)
Bis-GMA: bisphenol A diglycidyl dimethacrylate
TEGDMA: triethyleneglycol dimethacrylate
[2]Component (b) [acylphosphine oxide]
b$_1$: 2,4,6-trimethylbenzoyldiphenylphosphine oxide
b$_2$: 2,4,6-trimethylbenzoylphenylphosphinate ethyl ester The results in Table 5 above indicate that the polymerizable compositions containing the monomer (a), the acylphosphine oxide (b), the organic peroxide (c), the tertiary amine (d) and the aromatic sulfinic acid (salt) (e) for dental use in Examples 11 and 12 have far smaller light resistance values ($\Delta E_1$) than the value of the polymerizable composition with no acylphosphine oxide (b) contained therein for dental use in Comparative Example 7, showing that the compositions have excellent light resistance, and far smaller values ($\Delta E_2$) of the color change between prior to and after polymerization, showing that the compositions have excellent color stability, and smaller values of color fastness in hot water and in darkness ($\Delta E_3$), showing that the color of the compositions is less discolored in hot water and in darkness.

INDUSTRIAL APPLICABILITY

The polymerizable composition for dental use in accordance with the present invention exerts excellent curability by any of photo-polymerization and chemical polymerization.

Additionally, the polymerizable composition for dental use in accordance with the present invention has a color suitable for dental use, with less color change between prior to and after polymerization (prior to and after curing), excellent light resistance and penetrated less fading.

Furthermore, the polymerizable composition for dental use in accordance with the present invention can produce a cured product with a smaller thickness of the unpolymerized layer on the surface and high hardness, and can additionally produce a cured product with sufficient hardness and strength even in depth, because the composition has larger curing depth.

The polymerizable composition for dental use in accordance with the present invention additionally has excellent color fastness in hot water and in darkness, so that the composition is less discolored even if the composition is exposed to hot water in the oral cavity.

Still additionally, the polymerizable composition for dental use in accordance with the present invention has excellent adhesion to teeth and metals, and the composition has much more high adhesion to teeth in combination with an acid monomer with an acid group for a part of the monomer (a).

Accordingly, the polymerizable composition for dental use in accordance with the present invention may effectively be used for utilities, for example as bonding agents for dental use, such as resin cement and resin reinforced glass ionomer cement; composite resins for dental use and compomers for dental use, such as fissure restorative materials, support construction materials, sealant; adhesives for dental use, such as tooth bonding agents and adhesives for orthodontic devices; dental primers; and opaque primers.

For using the present polymerizable composition for dental use as a composite resin, in particular, even a deep cavity can be filled just once because the curing depth of the composition is large, so that a cured product with greater hardness is yielded even in such depth, effectively retaining aesthetic beauty with less discoloration.

When the present polymerizable composition for dental use is used as a bonding agent, the composition additionally has such greater surface curability that the wear of cement lines can be prevented, with less discoloration, which effectively works to retain aesthetic beauty.

When the present polymerizable composition for dental use is used as a dental adhesive, furthermore, the composition has such a larger polymerization rate that the application of the composition is simple, which works to readily promote treatment with other restorative materials such as composite resin.

When the present polymerizable composition for dental use is used as a dental primer, furthermore, the composition has such excellent curability when penetrated into teeth that it shows much improved adhesion to teeth.

What is claimed is:

1. A polymerizable composition for dental use, comprising monomer (a) with at least one polymerizable olefinic unsaturated group, acylphosphine oxide (b), organic peroxide (c), tertiary amine (d) and aromatic sulfinic acid and/or a salt thereof (e).

2. A polymerizable composition for dental use according to claim 1, comprising a monomer with at least one polymerizable olefinic unsaturated group and an acid group for a part of the monomer (a).

3. A polymerizable composition for dental use according to claim 1, wherein the organic peroxide (c) is separately packed from the tertiary amine (d) and the aromatic sulfinic acid or a salt thereof (e).

4. A polymerizable composition for dental use according to claim 1, comprising the acylphosphine oxide (b) within a range of 0.05 to 20% by weight, the organic peroxide (c) within a range of 0.05 to 20% by weight, the tertiary amine (d) within a range of 0. 5 to 10% by weight and the aromatic sulfinic acid and/or a salt thereof (e) within arange of 0.05 to 10% by weight.

5. A polymerizable composition for dental use according to claim 1, wherein the acylphosphine oxide (b) is benzoyldiphenylphosphine oxide and/or benzoylphenylphosphinate ester which may have or may not have substituent respectively and the organic peroxide (c) is diacylperoxide.

6. A polymerizable composition for dental use according to claim 1, wherein the acylphosphine oxide (b) is 2,4,6-trimethylbenzoyldiphenylphosphine oxide and/or 2,4,6-trimethylbenzoylphenylphosphinate alkyl ester and the organic peroxide (c) is benzoyl peroxide.

7. A polymerizable composition for dental use according to claim 1, wherein the monomer (a) is a (meth)acrylate monomer.

8. A polymerizable composition for dental use according to claim 1, comprising a filler a t a weight ratio of the monomer:the filler=99.9:0.1 to 10:90.

* * * * *